United States Patent [19]

Suzuki

[11] Patent Number: 5,610,152
[45] Date of Patent: Mar. 11, 1997

[54] ANTI-OBESITY AGENT 4-CHOLESTEN-3-ONE

[75] Inventor: Kunio Suzuki, Wako, Japan

[73] Assignee: Rikagaku Kenkyusho, Wako, Japan

[21] Appl. No.: 371,429

[22] Filed: Jan. 11, 1995

Related U.S. Application Data

[63] Continuation of Ser. No. 244,719, Jun. 17, 1994, Pat. No. 5,420,121.

[30] Foreign Application Priority Data

Dec. 20, 1991 [JP] Japan ................................. 3-338916

[51] Int. Cl.⁶ .................................................. A61K 31/56
[52] U.S. Cl. ........................... 514/177; 552/544; 552/601; 514/909
[58] Field of Search ............................. 514/177, 909; 552/544, 601

[56] References Cited

U.S. PATENT DOCUMENTS

| | | | |
|---|---|---|---|
| 4,003,794 | 1/1977 | Sugiura et al. ...................... | 195/66 R |
| 4,088,760 | 5/1978 | Benson et al. ....................... | 424/242 |

*Primary Examiner*—Theodore J. Criares
*Attorney, Agent, or Firm*—Oblon, Spivak, McClelland, Maier & Neustadt, P.C.

[57] ABSTRACT

The present invention provides an anti-obesity agent comprising 4-cholesten-3-one represented by the following formula:

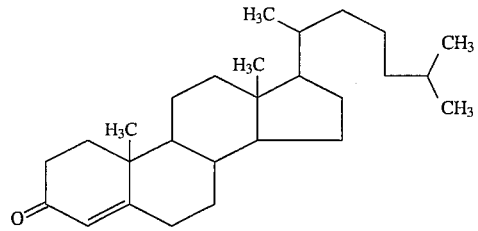

as an effective component. The anti-obesity agent of the present invention is useful because of inhibition effect of body weight increase and body fat accumulation. The present invention also provides a medicinal composition comprising 4-cholesten-3-one as an effective component and a pharmaceutically acceptable excipient as well as methods for preventing and treating obesity comprising administering an effective amount of 4-cholesten-3-one to a person.

4 Claims, 7 Drawing Sheets

FIG. 1

Time-course in Body Weights of CDF 1 Mice

FIG. 3

Organ Weight of CDF1 Mice (18-Month-Old)

FIG. 4

Organ Weight of CDF1 Mice (18-Month-old)−2

FIG. 6

Time-course in Body Weights of CDF 1 Mice

ANTI-OBESITY AGENT 4-CHOLESTEN-3-ONE

This is a Continuation of application Ser. No. 08/244,719 filed on Jun. 17, 1994, which was filed as International Application No. PCT/JP92/01642, now U.S. Pat. No. 5,420,121.

TECHNICAL FIELD

The present invention relates to an anti-obesity agent and more specifically to an anti-obesity agent comprising cholest-4-en-3-one (4-cholesten-3-one) as an effective component.

BACKGROUND ART

The obesity means such a body condition that adipose tissue (body fat) is systemically overaccumulated and results from an energy intake higher than the energy expenditure over a long period of time. The obesity is accompanied by the limitation in the physical activity and the application of an excess load to various internal organs and results in various associated diseases such as arteriosclerosis, cancers and diabetes mellitus to thus ruin the obese person's health.

Until now, there have been proposed a variety of medicinal-therapeutic methods for preventing obesity, but these methods must solve various difficulties in order to ensure a satisfactory effect. For instance, the drug therapy using hormones or excitometabolics suffers from a problem that the decomposition of body proteins are promoted simultaneously with the decomposition of body fats. Among the hormone, a certain androgenic hormone has been known to show anti-obesity effects through the stimulation of the myotropic action and hence the promotion of the consumption of reserve fats. Examples of such androgenic hormones include dehydroepiandrosterone and 3-keto-$\Delta^{\uparrow}$9–19-norsteroid (Japanese Un-examined Patent Publication No. Hei 02-275895). In addition, anorectics and digestive enzyme-inhibitors suffer from a problem of side-effects such as nervous sympton and diarrhea.

Accordingly, an object of the present invention is to provide an anti-obesity agent free of the foregoing disadvantages.

Another object of the present invention is to provide a medicinal composition effective for the prevention and treatment of obesity.

A still another object of the present invention is to provide a method for preventing obesity and treating patients suffering from obesity.

DISCLOSURE OF THE INVENTION

The inventor of this invention has found out that 4-cholesten-3-one has a fat accummulation-inhibitory effect and that obesity can be prevented and treated through the administration of this compound, and thus have completed the present invention.

According to an aspect of the present invention, there is provided an anti-obesity agent which comprises 4-cholesten-3-one as an effective component and which is effective for the prevention and treatment of obesity.

According to another aspect of the present invention, there is provided a medicinal composition which comprises 4-cholesten-3-one as an effective component and a pharmaceutically acceptable excipient and which is effective for the prevention and treatment of obesity.

According to a still another aspect of the present invention, there is provided a method for preventing obesity and for treating a patient suffering from obesity, characterized in that an effective amount of 4-cholesten-3-one is administered to a person.

The anti-obesity agent of the present invention is quite useful since it is substantially non-toxic.

BEST MODE FOR CARRYING OUT THE INVENTION

4-Cholesten-3-one may be chemically synthesized or may be produced starting from cholesterol as a substrate using cholesterol oxidase (cholesterol:oxigen oxidoreductase: EC1, 1, 3, 6) produced by *Brevibacterium sp.*, *Cullulomonas sp.*, *Nocardia erythropolis*, *Pseudomonas fluorescens*, *Schizophyllum commune*, *Streptomyces sp.*, *Mycobacterium cholesterolicum* or other microorganisms. Moreover, it is also possible to use commercially available ones produced by either of the foregoing methods.

The compound, 4-cholesten-3-one, is represented by the following formula (I) and has the following physical and chemical properties:

(1) Molecular Formula: $C_{27}H_{44}O$ (2) Molecular Weight: 384.65

(3) Melting Point (mp): 82° C.

(4) Specific Rotatory Power, $[\alpha]_D$: +88° (in chloroform)

(5) UV$\lambda_{max}$ (mn): 240, 320

(6) Solubility: The compound is hardly soluble in water; slightly soluble in alcohol; soluble in ether, chloroform, pyridine, benzene and petroleum ether; and also highly soluble in fats and oils.

(7) Taste.Odor.Color: The compound is a stable tasteless, odorless and achromatic crystal at ordinary temperature.

(8) CAS Number: CAS [601-57-0]

While not wanting to be bound by any particular theory, the mechanism whereby the compound 4-cholesten-3-one shows the anti-obesity effect will be assumed to be as follows. The fats ingested in the form of diets are taken in the interior of the spherical membrane of cylomicron, i.e., a lipoprotein in the small intestine and are then transferred to adipose tissues. On the other hand, the fats synthesized in the liver are taken in the interior of the spherical membrane of a VLDL (very low density lipoprotein) and then transferred to adipose tissues. These lipoproteins having a fat-transporting function such as cylomicron and VLDL each is formed from a membrane which comprises three components, i.e., cholesterol, phospholipids and apoproteins and serves to take lipids, i.e., triglyceride and cholesterol esters therein and to transport them to each tissue. As has been explained above, cholesterol is a principal constituent of the lipoprotein having a fat-transporting function. 4-Cholesten-3-one antagonizes the action of the cholesterol, thus inhibits the formation of the foregoing lipoprotein and, in turn, the transportation of the lipids and accordingly, shows the inhibition effect of body fat accumulation. As a result, the compound ensures the obesity-inhibitory effect. Alternatively, it is also assumed that 4-cholesten-3-one inhibits the formation of adrenal corticoid through the antagonistic action to that of the cholesterol and, in turn, inhibits the formation of fatty acids in the liver and as a result, the compound shows its anti-obesity effect.

Food products can be prepared using the anti-obesity agent of the present invention. When incorporating the agent into food products, 4-cholesten-3-one may directly be added to each food and alternatively, the compound is first added to fats and oils as starting materials for an intended food and then the food is prepared from the fats and oils. 4-Cholesten-3-one may be added to a food or fats and oils in an amount ranging from 1 to 5,000 mg per 100 g of foods or fats and oils. Moreover, 4-cholesten-3-one can be formulized into various pharmaceutical formulations such as solutions, suspensions, capsules, powder, granules, grains or tablets (pills) and these formulations may then be added to foods or fats and oils.

The anti-obesity agent of the present invention may also be formulated into medicinal preparations. In this case, the formulations may be administered through any route. They may be administered through, for instance, an oral, intravenous, intraperitoneal, subcutaneous or intramuscular route, with the administration through the oral route being preferred. In case of oral administration, 4-cholesten-3-one may be administered alone or in combination with pharmaceutically acceptable excipients in the form of various preparations such as solutions, suspensions, powder, granules, capsules or tablets. The excipients may be those commonly used, for instance, sugars such as lactose, sucrose and glucose; starches; inorganic substances such as calcium carbonate and calcium sulfate; crystalline cellulose, distilled water, purified water, sesame oil, soybean oil, corn oil, olive oil and cotton seed oil. When formulating the compound into preparations, various additives can be used and examples thereof include binders, lubricants, dispersants, suspending agents, emulsifiers, diluents, buffers, antioxidants and germicides. Moreover, appropriate buffers, isotonic solutions or the like may be added to the compound and then the resulting mixture is dissolved in, for instance, oils such as vegetable oils to give injectable solutions. 4-Cholesten-3-one may also be mixed with other medicines or may be used in combination therewith. In this respect, the foregoing pharmaceutical preparations may be subjected to a sterilization treatment.

The dose of the anti-obesity agent of the present invention varies depending on, for instance, ages, sexes, clinical sign, administration pathway, administration times per day, dosage forms, but the dose for adult desirably ranges from about 1 to 1,500 mg/kg body weight/day in terms of the weight of 4-cholesten-3-one, for the oral administration.

The present invention will hereunder be explained in more detail with reference to the following examples. These examples never limit the scope of the present invention, but are given for illustrating the present invention.

EXAMPLE 1

A. Test Method

1. Experimental Animals and Care Conditions

Male and female CDF1 mice (BALB/C×DBA/2 F1) of 4-week-old (available from Charles River Japan Inc.; 300 animals in all (150 males and females each)) were divided into three groups, i.e., 4-cholesten-3-one fed group, cholesterol fed group and untreated control group (each group being divided into two subgroups each comprising 50 male or 50 female animals). The following test was carried out using these 6 subgroups.

All of the mice were accommodated in aluminum cages (5 animals per cage) and bred for 17 months in an animal room at a temperature of 24±1° C. and a relative humidity of 55±5% and under 12:12 hr light/dark schedule. The cages and the bedding (White flake) were replaced with fresh ones every two days.

2. Preparation of Experimental Feed

The following test feeds 1) to 3) were prepared using a high fat commercial feed for breeding (type CMF, Oriental Yeast Co., Ltd., Tokyo) as a basal diet, formed into pellets and supplied to hoppers. Tap water as drink water was introduced into water bottle and the animals were allowed feed and water ad libitum. When the following feed 1) and 2) was used, the doses of 4-cholesten-3-one and cholesterol per mouse were about 650 mg/kg body weight/day, respectively.

1) Feed for the 4-Cholesten-3-One Fed Group: 4-Cholesten-3-one (available from Aldrich Chemical Co., U.S.A.) was added to the basal diet in an amount of 0.5% by weight based on the weight of the basal diet.

2) Feed for the Cholesterol Fed Group: Cholesterol (available from Aldrich Chemical Co., USA) was added to the basal feed in an amount of 0.5% by weight based on the weight of the basal feed.

3) Feed for the Untreated Control Group: Any additive was not added to the basal feed.

The CMF feed has the following composition: crude proteins 29.4%; crude fats 8.7%; minerals 6.5%; crude fibers 3.4%; soluble nitrogen-free extract 43.6%; and it has a moisture content of 8.4% and a calory of 370 Kcal/100 g. This is a feed having a fat content and a calory higher than those of the commercial feed which has a crude fats content of 4.4% and a calory of 343 Kcal/100 g.

3. Items to be Inspected (1) Determination of Changes in Body Weights

All of the surviving mice were examined for the body weights every months followed by calculation of the average value thereof for each group.

(2) Determination of Survival Rate

The number of surviving animals were determined every months to calculate the surviving rate. Moreover, the mice died were subjected to necropsy to inspect for tumor incidence and other lesions and the results obtained were recorded.

(3) Determination of Organ Weight

After 17 months of feeding, all the mice were sacrificed through anesthetizing them with carbon dioxide and animals free from any lesion were anatomized to inspect for tumor incidence and other lesions. In animals free from lesions, the weights of brain, lung, heart, liver, kidneys, spleen, testes (or ovaries), pituitary gland and adrenal gland, were measured and the average value thereof for each group was calculated.

(4) Determination of Amount of Abdominal Adipose Tissue

After 17 months of feeding, animals free from any lesion were examined for the amount of abdominal adipose tissue, followed by calculation of the average values thereof for each group.

(5) Determination of Rate of Tumor Incidence

After 17 months of feeding, all the mice were sacrificed through anesthetizing them with carbon dioxide and the number of animals suffering from tumor was scored.

B. Test Results (1) Determination of Changes in Body Weights

Figure 1:
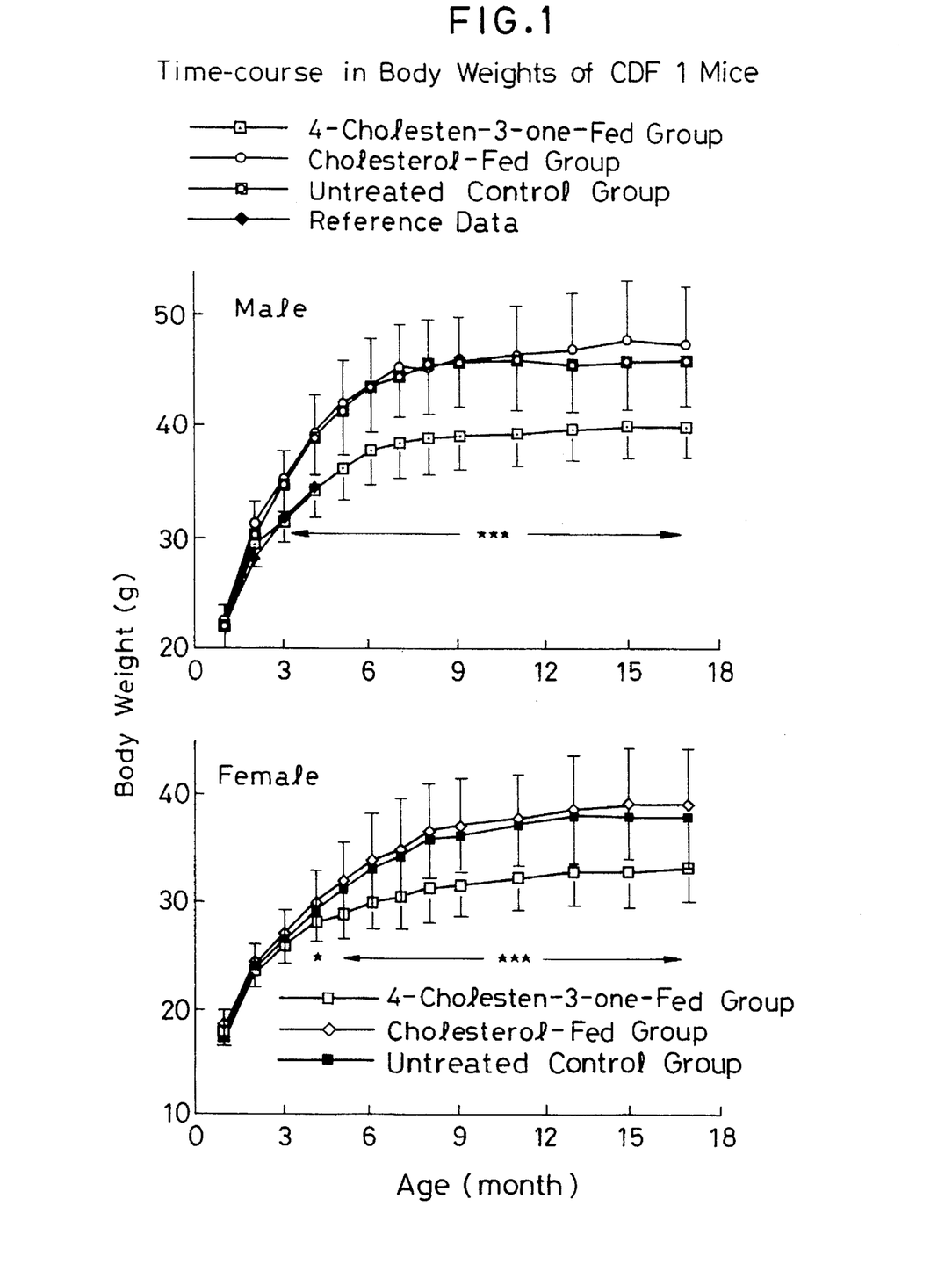
FIG. 1 shows time-course in the averaged body weight of CDF1 mice in each group.

Time-course of the averaged body weight of each group is plotted on FIG. 1 together with the reference data. Each value plotted on FIG. 1 is expressed in terms of the average value±standard deviation. The symbol: ★ means that the probability (p) in the result of the student t-test is less than 0.05 and the symbol: ★★★ means that p is less than 0.001.

One month after the initiation of the experiment, the body weights of the 4-cholesten-3-one fed groups (both male and female groups) were found to be lower than those observed for the untreated control groups and the difference therebetween was increased as the time proceeded. After 4 months, the body weight of the 4-cholesten-3-one fed group (male subgroup) was 13% smaller than that of the control group and thereafter the difference therebetween varied between 13 and 15%, while the body weight of the 4-cholesten-3-one fed group (female subgroup) was 12% smaller than that of the control group after 6 months and the difference therebetween then varied between 12 and 14%.

The body weights of the cholesterol fed groups (both male and female groups) were almost identical to those observed for the untreated control groups, but they were apt to increase as the time proceeded, as compared with those of the control groups.

The reference data for male animals are those reported by Morisada et al. (Jpn. J. Cancer Res., 1989, 80, pp. 77–82), i.e., the averaged body weights of the CDF1 mice (available from Charles River Japan Inc.) which were bred and raised up to 4-month-old using the commercial stock feed. These data are almost identical to those observed for the 4-cholesten-3-one fed groups.

The male and female mice in the 4-cholesten-3-one fed groups were normally raised in their appearance, while the mice of the cholesterol fed and untreated control groups had clearly corpulent figures.

The foregoing results indicate that the body weights of the cholesterol fed and untreated control groups were increased obesely due to feeding of high energy foods, while the 4-cholesten-3-one fed groups were normally raised and bred.

(2) Determination of Survival Rate

Figure 2:
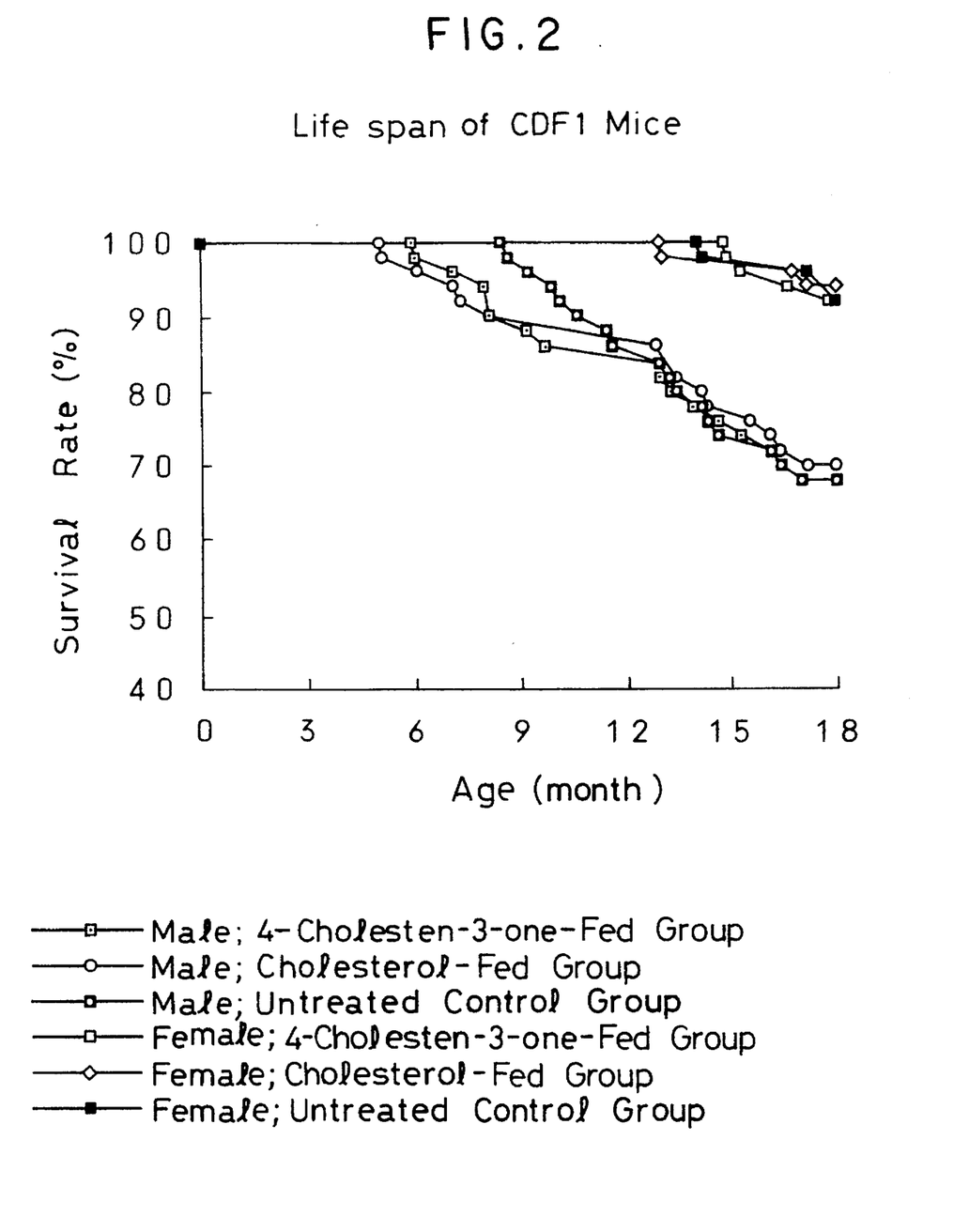
FIG. 2 shows the relation between the monthly age and the survival rate of CDF1 mice in each group.

The mortality curve observed for each group is shown in FIG. 2.

There is not observed any significant difference in the survival rate between the groups tested (including both male and female subgroups) up to 18-month-old.

This fact indicates that the feeding of 4-cholesten-3-one does not affect the mortality and that it is believed to be nontoxic.

(3) Determination of Organ Weight

Figure 3:
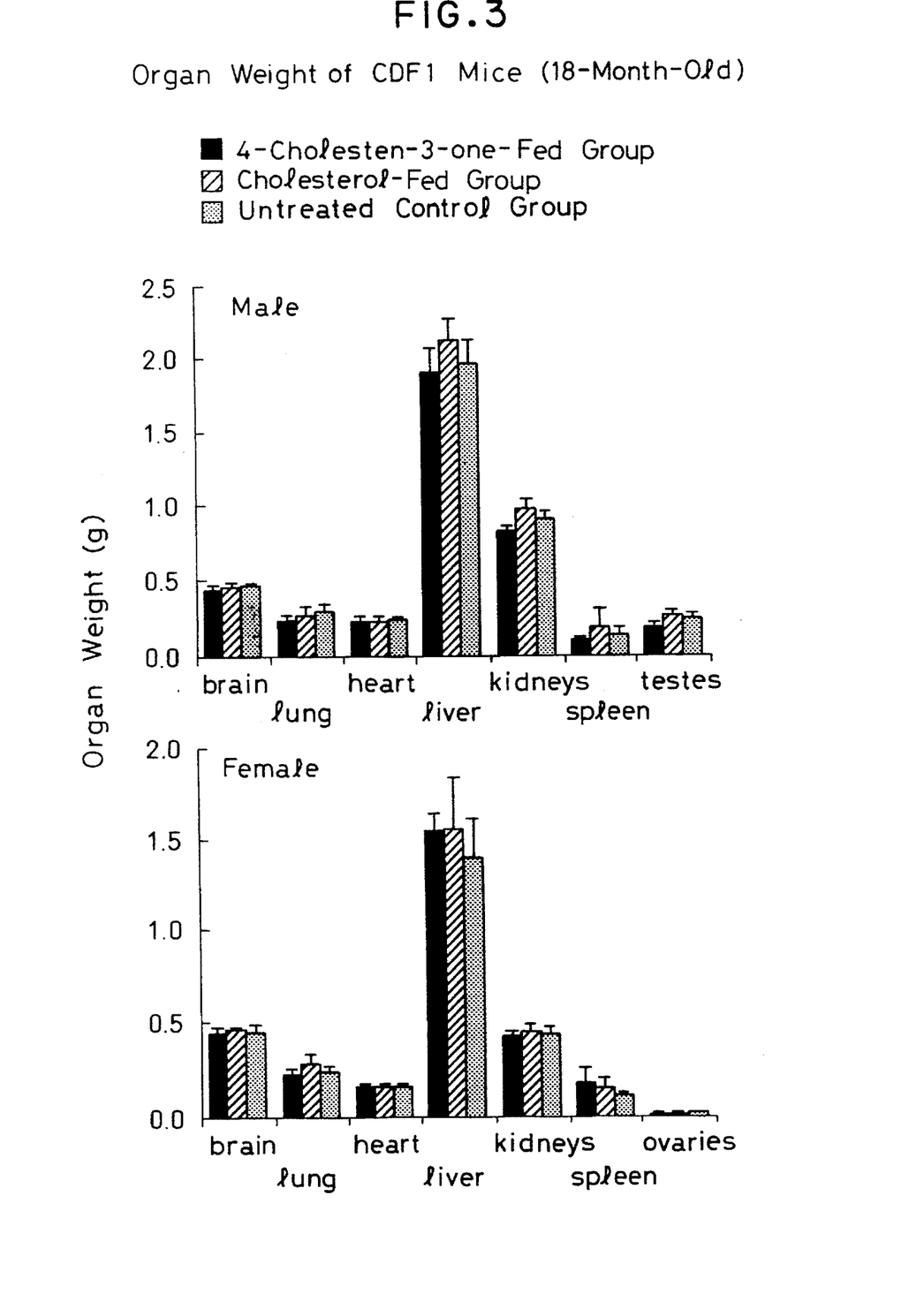
FIG. 3 shows the averaged weights of the organs, i.e., brain, lung, heart, liver, kidneys, spleen and testes (or ovaries) of CDF1 mice of 18-month-old in each group.
Figure 4:
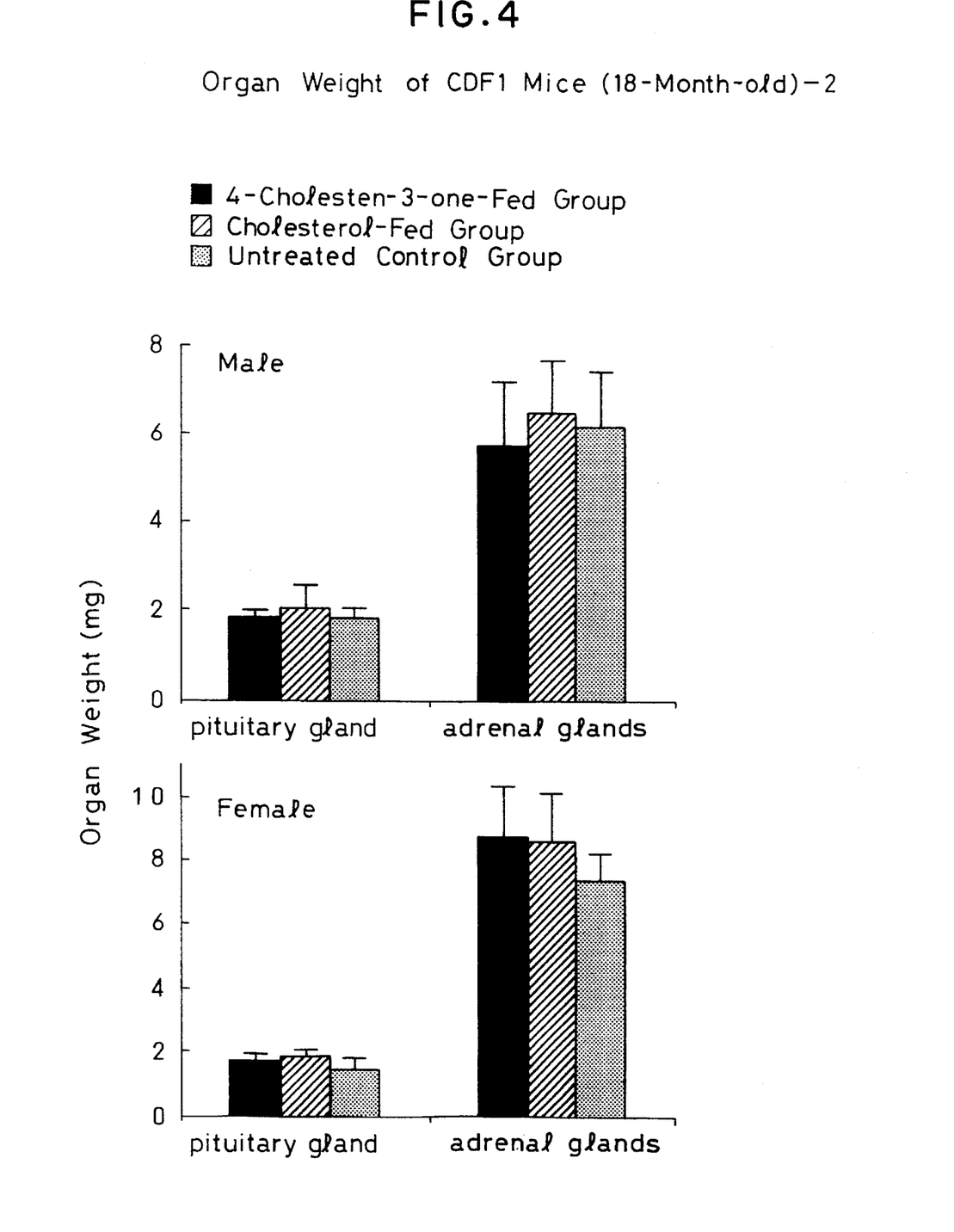
FIG. 4 shows the averaged weights of the organs, i.e., pituitary gland and adrenal gland of CDF1 mice of 18-month-old in each group.

The averaged weights of these organs observed for each group are plotted on FIGS. 3 and 4.

There was not any significant difference in the weight of each organ, i.e., brain, lung, heart, liver, kidneys, spleen or testes (or ovaries) between the groups (including both male and female subgroups). Moreover, there was not likewise observed any significant difference in the weights of the hormone-producing organs, i.e., pituitary gland and adrenal gland, between the groups (including both male and female subgroups).

As seen from these facts, the feeding of 4-cholesten-3-one did not adversely affect the growth and functions of each organ.

(4) Determination of Amount of Abdominal Adipose Tissue

Figure 5:
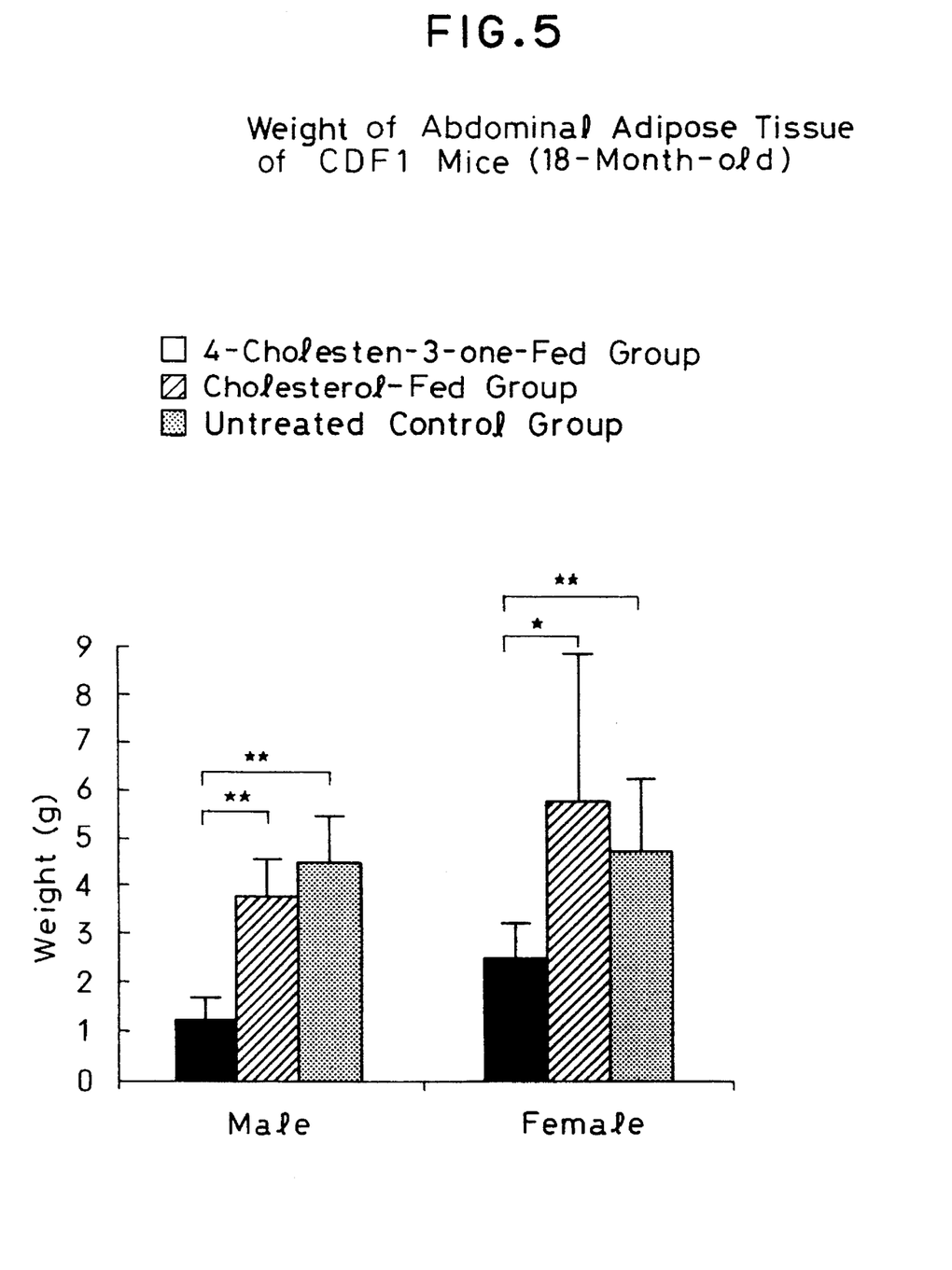
FIG. 5 shows the averaged amount of fats present in abdominal adipose tissues of CDF1 mice of 18-month-old in each group.

The averaged amount of the abdominal adipose tissue observed for each group is shown in FIG. 5. Each value in FIG. 5 is expressed in terms of the average value±standard deviation. The symbol: ★ means that the probability (p) in the result of the student t-test is less than 0.05 and the symbol: ★★ means that p is less than 0.01.

The averaged amount of the abdominal adipose tissue observed for the 4-cholesten-3-one fed group was about ⅓ time those observed for the untreated control and cholesterol fed groups for the male subgroups and about ½ time those observed for the untreated control and cholesterol fed groups for the female subgroups.

In addition, the untreated control and cholesterol fed groups had subcutaneous fats of back and abdominal regions, while the 4-cholesten-3-one fed group had only a slight subcutaneous fats of these regions (data are not shown).

It can be concluded that the feeding of 4-cholesten-3-one inhibits the body fat accumulation in abdominal and subcutaneous and prevents obesity.

(5) Determination of Rate of Tumor Incidence

The numbers of tumorous incidence formed in animals of each group are listed in the following Table 1.

TABLE 1

Tumor Incidence in CDF1 Mice

| Group | Sex | No. of animals[a] | Number of mice with tumor | | | |
|---|---|---|---|---|---|---|
| | | | Small Intestine | Lung | Liver | Spleen |
| 4-cholesten-3-one fed | male | 34 | 17(50)[b] | 6 | 2 | 0 |
| | female | 45 | 20(44) | 0 | 0 | 2 |

TABLE 1-continued

Tumor Incidence in CDF1 Mice

| group | | | | | | |
|---|---|---|---|---|---|---|
| cholesterol | male | 34 | 15(44) | 8 | 3 | 2 |
| fed group | female | 46 | 14(30) | 1 | 1 | 2 |
| untreated | male | 35 | 24(69) | 9 | 0 | 1 |
| control | female | 47 | 17(36) | 5 | 1 | 0 |
| group | | | | | | |

| | | Number of mice with tumor | | | |
|---|---|---|---|---|---|
| Group | Sex | Sexual Organ | others | Total Number | Lymphoma |
| 4-cholesten-3- | male | 0 | 1 | 19(56) | 1 |
| one fed group | female | 1 | 0 | 20(44) | 3 |
| cholesterol | male | 0 | 0 | 18(52) | 0 |
| fed group | female | 3 | 0 | 17(37) | 2 |
| un-treated | male | 0 | 0 | 26(74) | 1 |
| control | female | 5 | 1 | 23(49) | 2 |
| group | | | | | | |

[a] Number of mice suviving month on 18;
[b] The numerical value in the parentheses represents percentage.

In either of the groups, the small intestinal polyposis (one of benign tumors) are observed in a high incidence which is not less than 40% for male mice and not less than 30% for female mice, but any significant difference in the incidence between the groups tested was not observed at all. In respect of tumors formed in sites such as lung, liver, spleen, sexual organs and other sites, there was not observed any characteristic tendency in every groups. Moreover, the overall incidence of tumors for the male mice was greater than that observed for the female mice, but any significant difference in the incidence between the groups tested was not observed at all.

It can be concluded, from the foregoing facts, that the feeding of 4-cholesten-3-one (about 650 mg/kg body weight/day) does not show any carcinogenicity and tumor promoting activity. It has been reported that the small intestinal polyposis are developed at rates of 51% and 37% for male and female BALB/c mice of 12-month-old, the female BALB/c mice being the mothers of the CDF1 mice (Mizutani et al., Cancer Lett., 1984, 25, pp. 19–23). Accordingly, the incidence of small intestinal polyposis would be high in all of the groups tested for the reason that the polyposis would be inherited in the CDF1 mice.

Furthermore, there was not observed any characteristic difference, between the groups tested, in the development of diseases or lesions other than tumors.

EXAMPLE 2

A. Test Method

1. Experimental Animals and Care Conditions

Male and female CDF1 mice of 5-week-old (available from Charles River Japan Inc.; 60 animals in all) were divided into six groups (30 animals each), i.e., male and female groups to which the common feed was fed (hereunder referred to as "common feed fed group"), male and female groups to which a feed having a high fat content was fed (hereunder referred to as "high fat feed fed group") and male and female groups to which a feed having a high fat content and containing 4-cholesten-3-one was fed (hereunder referred to as "4-cholesten-3-one fed group"), each group comprising 10 mice. All of the mice were accommodated in aluminum cages (5 animals per cage) and bred for 13 days in an animal room at a temperature of 24±1° C. and a relative humidity of 50±5% and under 12:12 hr light/dark schedule. The cages and the bedding were replaced with fresh ones every two days.

2. Preparation of Experimental Feed

The following test feeds 1) to 3) (mash feeds) were prepared using a modified AIN-formula-purified diet (Oriental Yeast Co., Ltd., Tokyo) as a basal diet and supplied to hoppers. Tap water as drink water was introduced into water bottle and the animals were allowed feed and water ad libitum.

1) Feed for Stock Feed Fed Group: The basal feed as such was used. The fat content thereof was found to be 6%.

2) Feed for High Fat Feed Fed Group: Soybean oil was added to the basal feed in an amount of 11.5 g per 100 g of the latter to adjust the fat content thereof to 15%.

3) Feed for 4-Cholesten-3-One Fed Group: To the feed for the high fat feed fed group, there was added 4-cholesten-3-one (available from Aldrich Chemical Co., U.S.A.) to a concentration of 1%. The fat content thereof corresponds to 14.8%.

The modified AIN-formula-purified diet has the following composition: corn starch 41.5%; casein 25%; α-starch 10%; cellulose powder 8%; soybean oil 6%; minerals (AIN-76) 3.5%; granulated sugar 5%; and vitamins (AIN-76 and choline bitartrate) 1%.

3. Items to be Inspected (1) Determination of Changes in Body Weights

The mice were examined for the body weights at 6th and 13th day, followed by calculation of the average value thereof for each group. Each feed was replaced with fresh one every two days and at this stage, the remaining feed was weighed to calculate the amount of feed intake.

(2) Autopsy and Analysis of Lipids in Serum

After breeding over 13 days, all of the mice were sacrified using carbon dioxide and then the autopsy and the analysis of lipids in the sera were carried out.

B. Test Results (1) Determination of Changes in Body Weights

Figure 6:
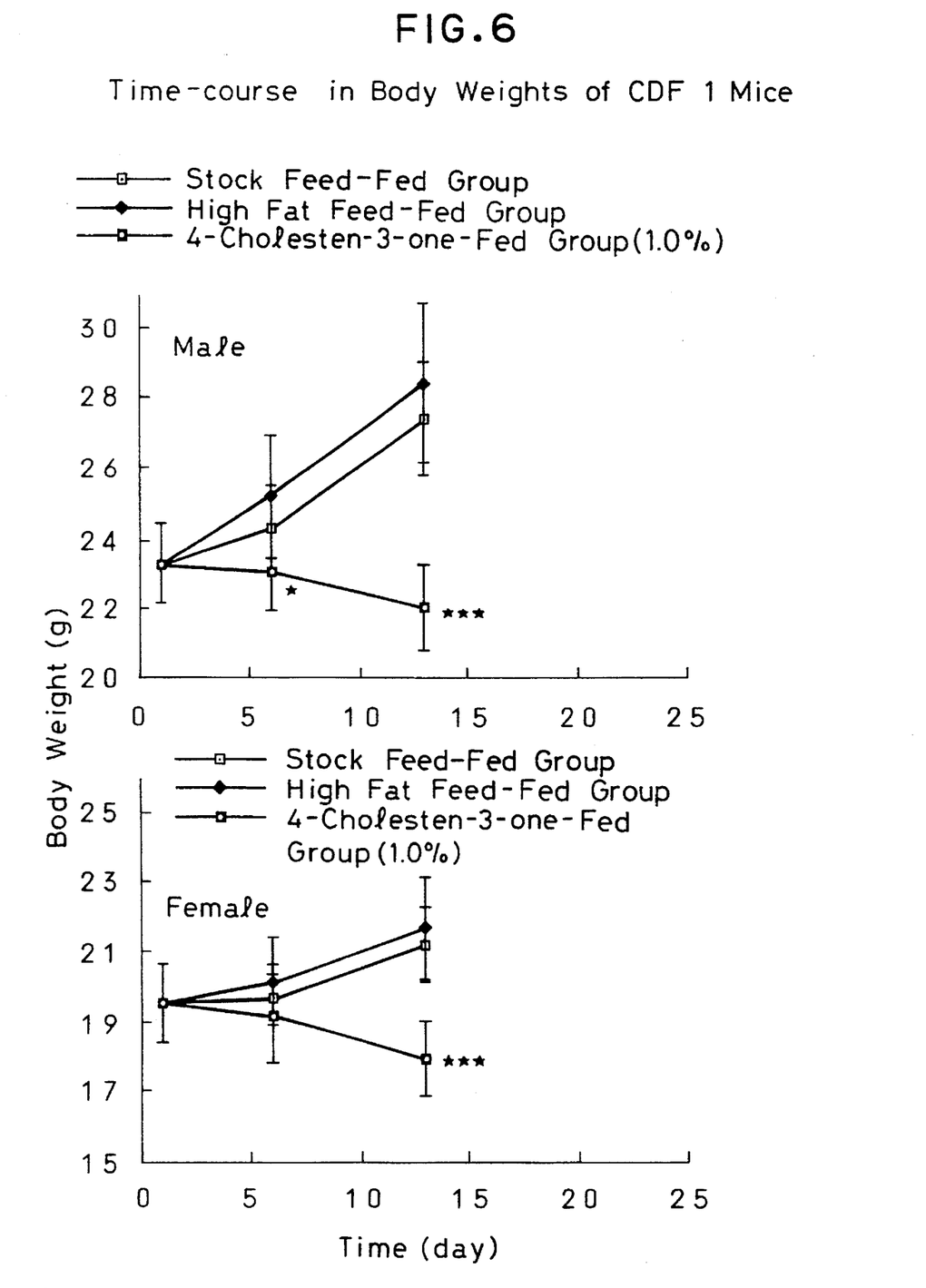
FIG. 6 shows time-course in the averaged body weight of CDF1 mice in each group.

The variation of the averaged body weight of each group is plotted on FIG. 6. Each value plotted on FIG. 6 is expressed in terms of the average of 10 animals in each group±standard deviation. The symbol: ★ means that the probability (p) in the result of the student t-test is less than 0.05 and the symbol: ★★★ means that p is less than 0.001. The common feed fed group and the high fat feed fed group showed constant increases in the body weights, while the 4-cholesten-3-one fed group did not show any increase in the body weight and the body weights thereof was rather apt to decrease. In case of the male mice, there was soon observed a statistically significant difference (p<0.05), even after 6 days, between the 4-cholesten-3-one fed group and the other two groups. In case of the female mice, the same phenomenon as that for the male mice was likewise observed, but the difference increased gradually over the entire test period.

The rates of feed intake, as expressed in terms of the weight (g)/animal/day, were found to be 4.20 for the stock feed fed group, 4.25 for the high fat feed fed group and 4.38 for the 4-cholesten-3-one fed group, respectively and were thus approximately identical to one another. The amount of 4-cholesten-3-one fed to the corresponding group was calculated on the basis of the rate of feed intake thus determined and found to be about 2,100 mg/kg body weight/day.

The mice in either of the test groups were visually active and there were not any clinical signs such as coat roughness and diarrhea.

(2) Autopsy and Analysis of Lipids in Serum

As a result of the autopsy, there were not observed any abnormalities such as hypertrophy, atrophy and color tone change of the major organs, i.e., lung, heart, liver, kidneys, spleen and testes (or ovaries) as well as adrenal glands in all of the groups tested.

Figure 7:
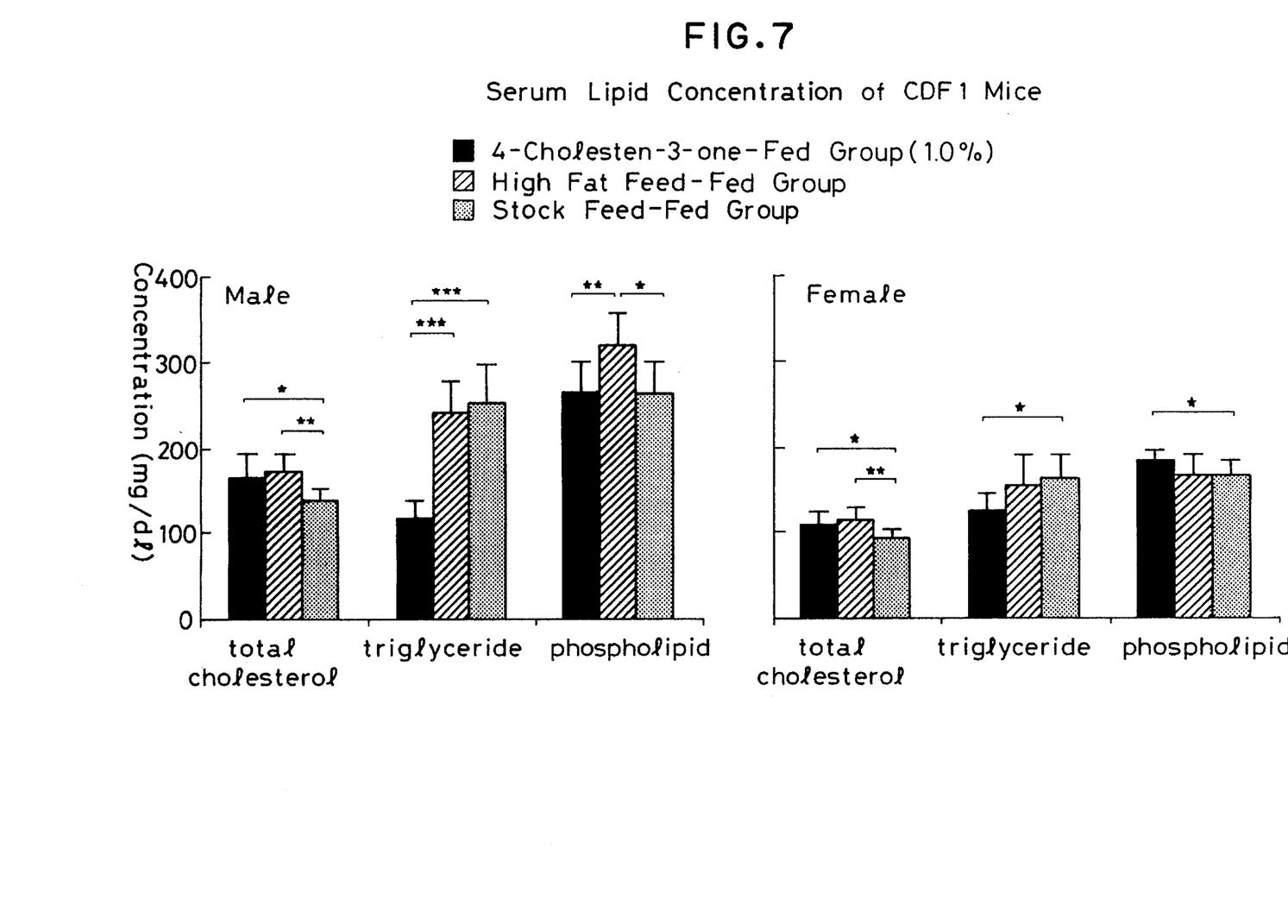
FIG. 7 shows the averaged values of serum lipids of CDF1 mice in each group.

The results of the analysis of serum lipids are shown in FIG. 7. Each value shown in FIG. 7 is expressed in terms of the average of 10 animals in each group±standard deviation. The symbol: ★ means that the probability (p) in the result of the student t-test is less than 0.05, the symbol: ★★ means that p is less than 0.01 and the symbol: ★★★ means that p is less than 0.001. The triglyceride content in the serum was decreased in the 4-cholesten-3-one fed group and this tendency was particularly conspicuous in the male mice. On the other hand, the total cholesterol content in the serum observed for the 4-cholesten-3-one fed group was slightly greater than that observed for the stock feed fed group and was almost identical to that observed for the high fat feed fed group. The phospholipid values in the sera observed for the 4-cholesten-3-one fed group and the stock feed fed group were approximately identical to one another for the male mice, while those observed for the female mice were slightly higher than those observed for the male mice, but there was not observed any statistically significant tendency.

The foregoing indicates that the body weights of the CDF1 mice were not increased, but decreased through addition of 1% 4-cholesten-3-one to the feed and that the triglyceride values in the sera of the CDF1 mice were also reduced. It was also found that the body weight-controlling effect of 4-cholesten-3-one was independent of the difference in the amount of the feed intake. Moreover, 4-cholesten-3-one was found to be substantially non-toxic.

INDUSTRIAL APPLICABILITY

The anti-obesity agent of the present invention is useful because of inhibition effect of the body weight increase and body fat accumulation. Moreover, the anti-obesity agent of the present invention is substantially non-toxic and can inhibit the body fat accumulation and in turn can prevent or treat obesity even when high energy foods are taken. The anti-obesity agent of the invention is also useful since the prevention or treatment of the obesity with the anti-obesity agent of the present invention would permit the prevention of various diseases such as arteriosclerosis, cancers and diabetes mellitus associated with the obesity.

I claim:

1. An anti-obesity food composition comprising from 1 to 5,000 mg of 4-cholesten-3-one per 100 g of said food.

2. A medicinal composition comprising an anti-obesity effective amount of 4-cholesten-3-one and a pharmaceutically acceptable excipient.

3. The food composition of claim 1 further comprising fat and protein.

4. The food composition of claim 1, wherein the concentration of 4-cholesten-3-one is 0.5–1%.

* * * * *